(12) United States Patent
Dacosta et al.

(10) Patent No.: US 9,949,773 B2
(45) Date of Patent: Apr. 24, 2018

(54) ORTHOPEDIC BONE PLATE AND LOCKING TAB APPARATUS AND METHOD OF USE

(71) Applicant: PARAGON 28, INC., Englewood, CO (US)

(72) Inventors: Albert Dacosta, Lone Tree, CO (US); Thomas Sangiovanni, Miami, FL (US); Michael Houghton, Fort Collins, CO (US)

(73) Assignee: PARAGON 28, INC., Englewood, CO (US)

( * ) Notice: Subject to any disclaimer, the term of this patent is extended or adjusted under 35 U.S.C. 154(b) by 185 days.

(21) Appl. No.: 14/655,929

(22) PCT Filed: Jul. 3, 2014

(86) PCT No.: PCT/US2014/045446
§ 371 (c)(1),
(2) Date: Jun. 26, 2015

(87) PCT Pub. No.: WO2015/094410
PCT Pub. Date: Jun. 25, 2015

(65) Prior Publication Data
US 2015/0335366 A1 Nov. 26, 2015
US 2017/0151002 A9 Jun. 1, 2017

Related U.S. Application Data

(63) Continuation-in-part of application No. PCT/US2013/077173, filed on Dec. 20, 2013.
(Continued)

(51) Int. Cl.
*A61B 17/80* (2006.01)
(52) U.S. Cl.
CPC .......... *A61B 17/8095* (2013.01); *A61B 17/80* (2013.01); *A61B 17/809* (2013.01)

(58) Field of Classification Search
CPC ............ A61B 17/8061; A61B 17/8071; A61B 17/809; A61B 17/8095
See application file for complete search history.

(56) References Cited

U.S. PATENT DOCUMENTS 5,549,612 A * 8/1996 Yapp .................. A61B 17/7059
411/200
5,662,655 A 9/1997 Laboureau et al.
(Continued)

FOREIGN PATENT DOCUMENTS

DE 202011050305 U1 7/2011
EP 1356778 A2 10/2003
(Continued)

OTHER PUBLICATIONS

International Preliminary Report on Patentability for International Application No. PCT/US2014/045446 dated Jun. 21, 2016.
(Continued)

*Primary Examiner* — Nicholas Woodall
(74) *Attorney, Agent, or Firm* — Heslin Rothenberg Farley & Mesiti P.C.

(57) ABSTRACT

The present invention discloses an orthopedic bone plate and locking tab apparatus and method of use. The orthopedic plate includes a body with a first end, a second end, and a central portion extending between the first end and the second end, a first pair of lobes at the first end, a second pair of lobes at the second end, and a securing mechanism extending away from a bottom surface of the central portion. The securing mechanism includes a base portion projecting from the body portion of the bone plate and two opposing extension members projecting from the base portion. A method for inserting the bone plate is also disclosed.

18 Claims, 13 Drawing Sheets

Related U.S. Application Data

(60) Provisional application No. 61/746,901, filed on Dec. 28, 2012.

(56) References Cited

U.S. PATENT DOCUMENTS

| | | | |
|---|---|---|---|
| 6,416,528 B1 | 7/2002 | Michelson et al. | |
| 6,565,570 B2* | 5/2003 | Sterett | A61B 17/8095 606/280 |
| 6,746,450 B1* | 6/2004 | Wall | A61B 17/7059 606/280 |
| 2003/0199875 A1 | 10/2003 | Mingozzi et al. | |
| 2003/0225409 A1 | 12/2003 | Freid et al. | |
| 2005/0085814 A1 | 4/2005 | Sherman et al. | |
| 2006/0235403 A1* | 10/2006 | Blain | A61B 17/7059 606/249 |
| 2007/0073298 A1 | 3/2007 | Beutter et al. | |
| 2009/0018543 A1* | 1/2009 | Ammann | A61B 17/8095 606/87 |
| 2009/0287249 A1* | 11/2009 | Reynolds | A61B 17/7059 606/246 |
| 2010/0152737 A1 | 6/2010 | Ralph et al. | |
| 2011/0087229 A1 | 4/2011 | Kubiak | |
| 2011/0106159 A1 | 5/2011 | Nazeck | |
| 2012/0184959 A1 | 7/2012 | Price et al. | |

FOREIGN PATENT DOCUMENTS

| | | |
|---|---|---|
| FR | 2785519 A1 | 5/2000 |
| WO | 2005060846 A1 | 7/2005 |
| WO | 2013062621 A2 | 5/2013 |

OTHER PUBLICATIONS

Jun. 30, 2015: International Report on Patentability for International Application No. PCT/US2013/077173.

International Search Report for PCT/US2014045446 dated Nov. 25, 2014.

International Search Report for PCT/US2013/077173 dated Apr. 3, 2014.

Extended European Search Report issued in European Patent Application No. 13867379.3 dated Sep. 2, 2016.

Extended European Search Report issued in European Patent Application No. EP 14870973.6 dated Jul. 13, 2017.

* cited by examiner

ORTHOPEDIC BONE PLATE AND LOCKING TAB APPARATUS AND METHOD OF USE

CROSS-REFERENCE

This application is a National Stage application based on International Application No. PCT/US2014/045446 filed on Jul. 3, 2014, published as WO 2015/094410 A1 on Jun. 25, 2015. This application also claims priority benefit to International Application No. PCT/US2013/77173 filed Dec. 20, 2013, which claims priority benefit under 35 U.S.C. § 119(e) of U.S. provisional application No. 61/746,901 filed Dec. 28, 2012, which are incorporated herein by reference in their entireties.

FIELD OF THE INVENTION

The present invention relates generally to the field of orthopedics related to an orthopedic bone plate and locking tab apparatus.

SUMMARY OF THE INVENTION

The present invention is directed toward devices and methods for securing an orthopedic bone plate over an osteotomy.

In one aspect of the present invention provided herein is an orthopedic bone plate including a body with a first end, a second end, and a central portion extending between the first end and the second end. The orthopedic bone plate may also include a first pair of lobes at the first end and a second pair of lobes at the second end. In addition, the orthopedic bone plate may include a securing mechanism extending away from a bottom surface of the central portion.

In another aspect of the present invention provided herein is a bone plate securing mechanism that is secured to a bone plate including a body portion with at least two attachment openings. The bone plate securing mechanism includes a base portion projecting away from the body portion of the bone plate and two opposing extension members projecting from the base portion.

In yet another aspect of the present invention provided herein is a method for inserting a bone plate. The method includes obtaining the bone plate. The bone plate including a body with a first end, a second end, and a central portion extending between the first end and the second end, a first pair of lobes at the first end, a second pair of lobes at the second end, and a securing mechanism projecting from a bottom surface of the central portion. The method also includes making an incision in a patient over at least one bone requiring correction. The method further includes performing an osteotomy on the at least one bone to form a first bone portion and a second bone portion. In addition, the method may include repositioning the first bone portion. Further, the method includes inserting the securing mechanism of the bone plate between the first bone portion and the second bone portion. The method may also include positioning the bone plate between the first bone portion and the second bone portion. The method may include securing the first end of the bone plate to the first bone portion. Further, the method may include moving the first bone portion and the second bone portion to a desired position to engage the securing mechanism. In addition, the method may include securing the second end of the bone plate to the second bone portion. The method may finally include closing the incision in the patient.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the invention.

DETAILED DESCRIPTION FOR CARRYING OUT THE INVENTION

Generally stated, disclosed herein are embodiments of orthopedic bone plates as well as securing mechanisms. Further, a surgical method for using the orthopedic bone plates is discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 1:
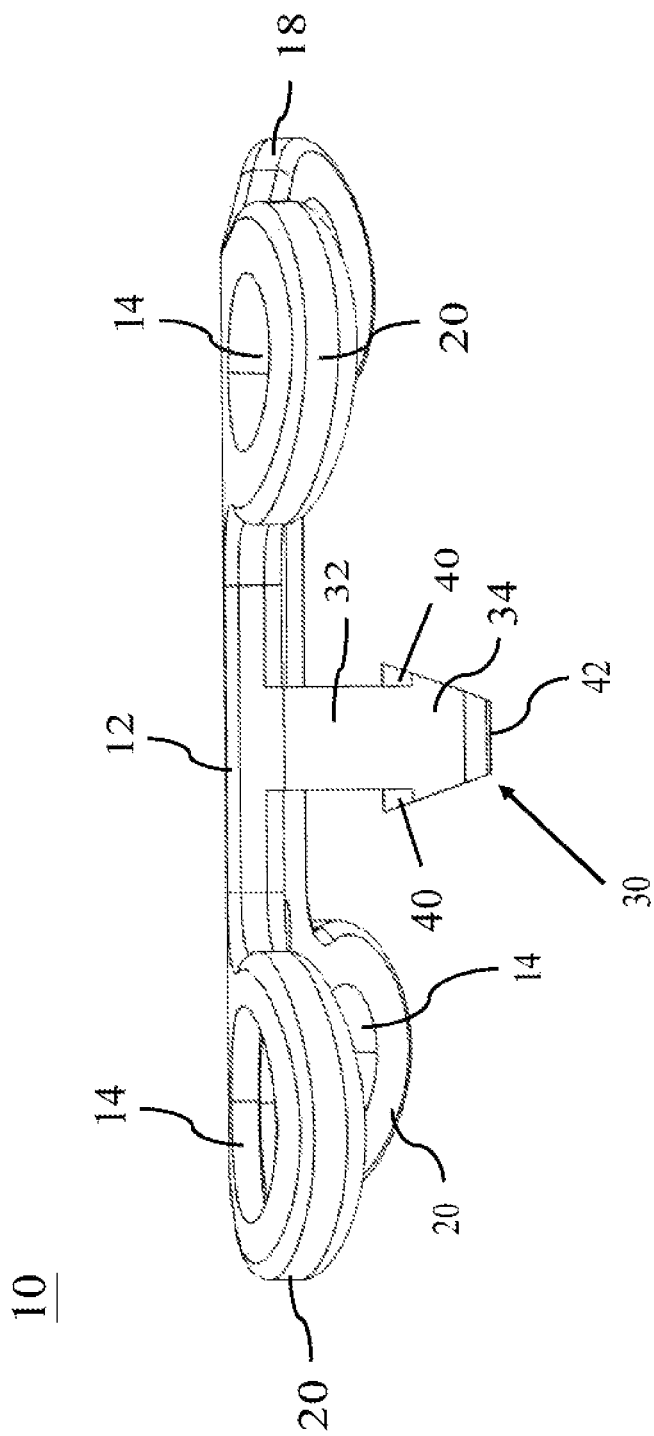
FIG. 1 is a lateral view of an orthopedic bone plate, in accordance with an aspect of the present invention.
Figure 2:
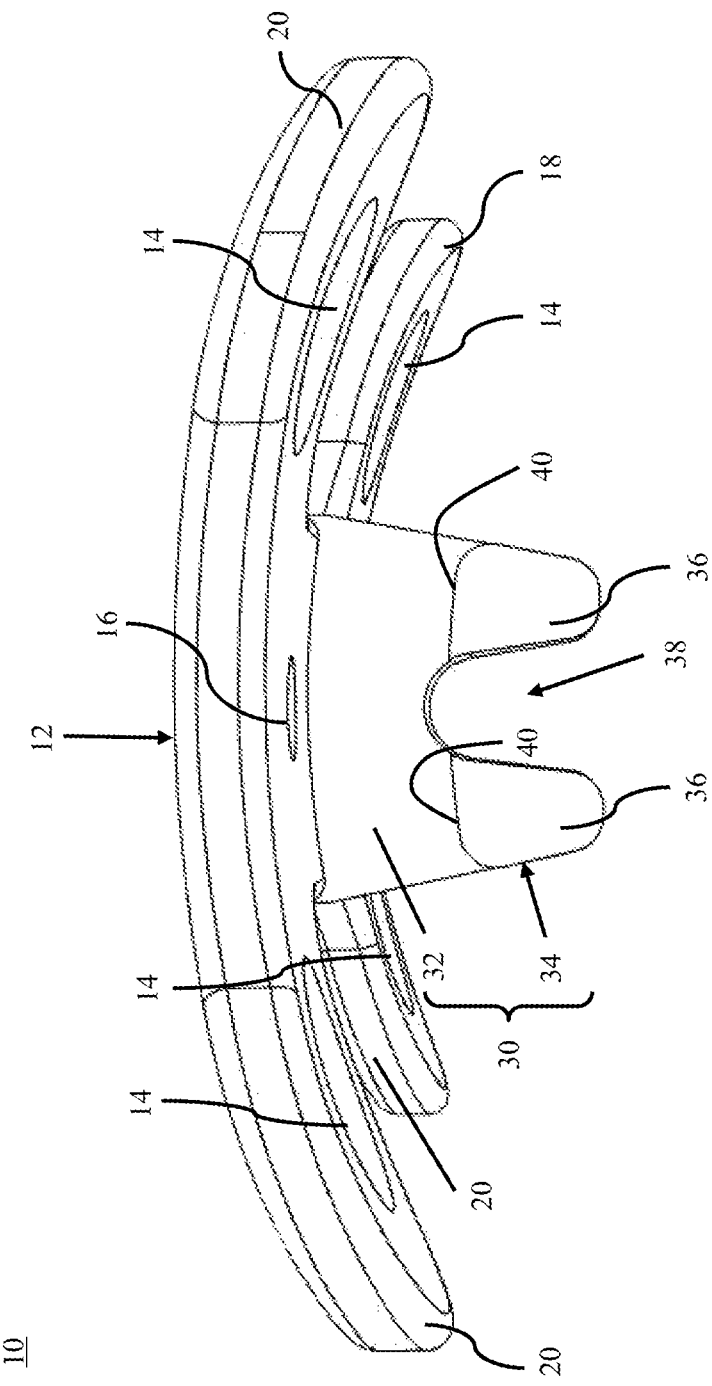
FIG. 2 is an end perspective view of the plate of FIG. 1, in accordance with an aspect of the present invention.
Figure 3:
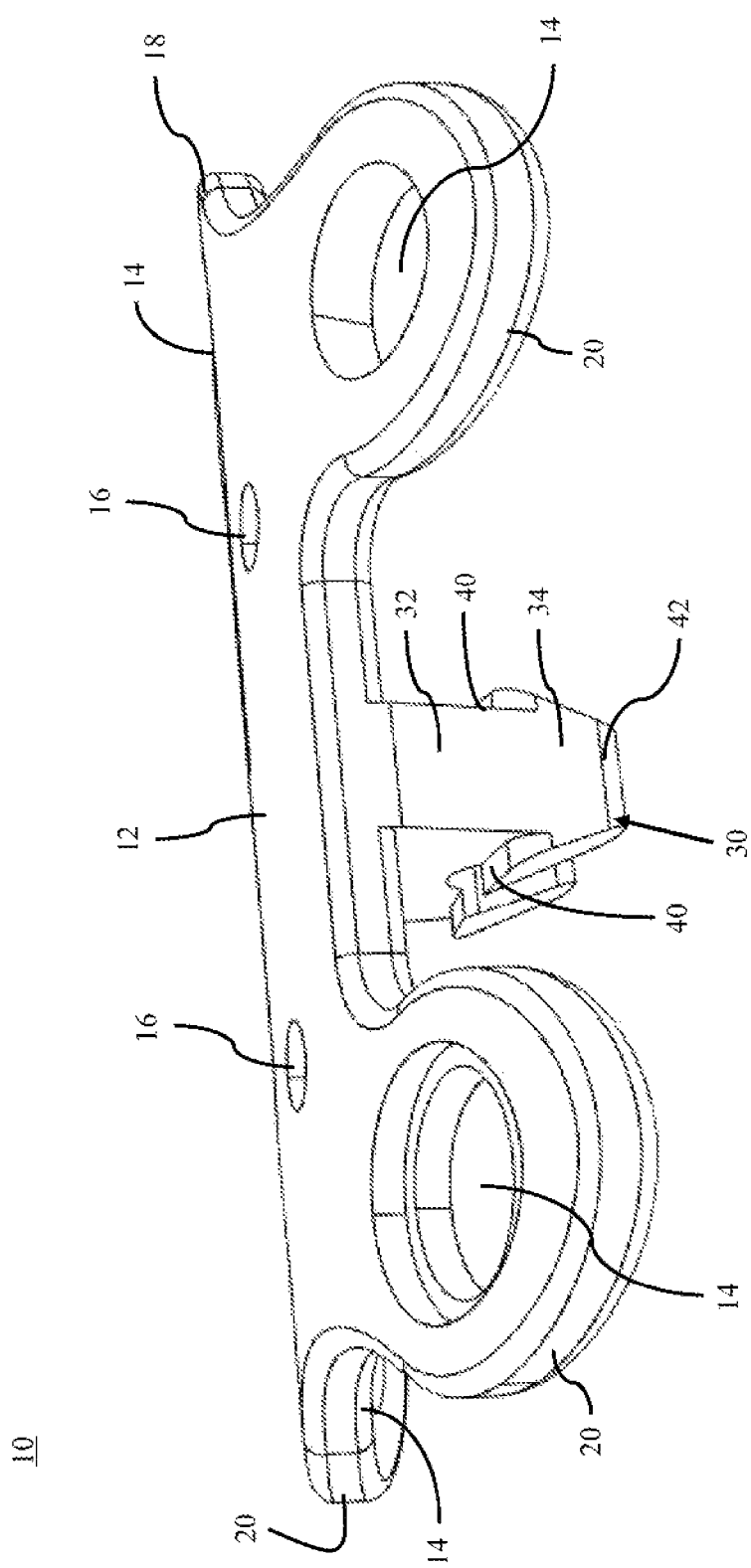
FIG. 3 is a lateral perspective view of the plate of FIG. 1, in accordance with an aspect of the present invention.
Figure 4:
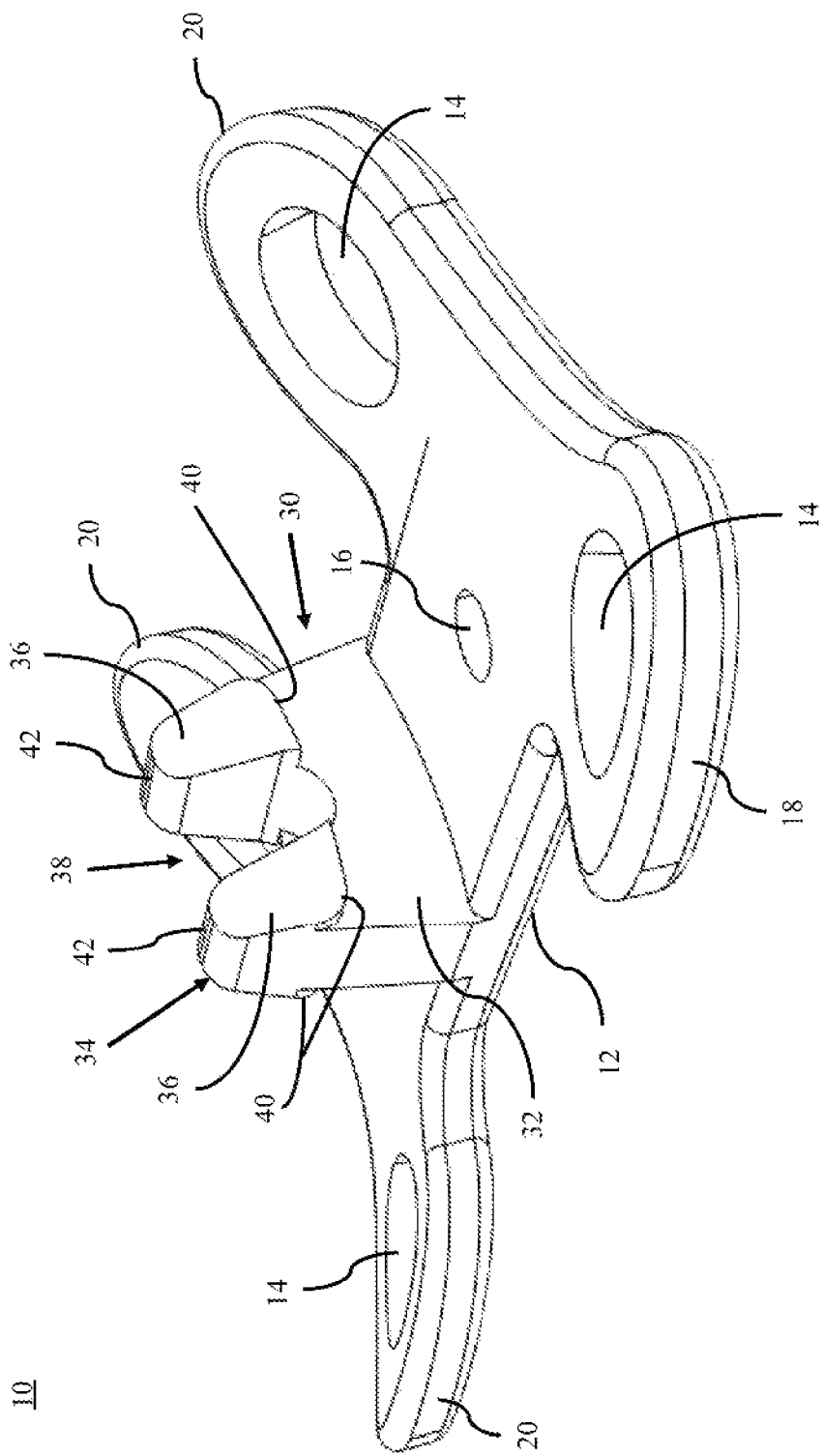
FIG. 4 is a bottom perspective view of the plate of FIG. 1, in accordance with an aspect of the present invention.
Figure 5:
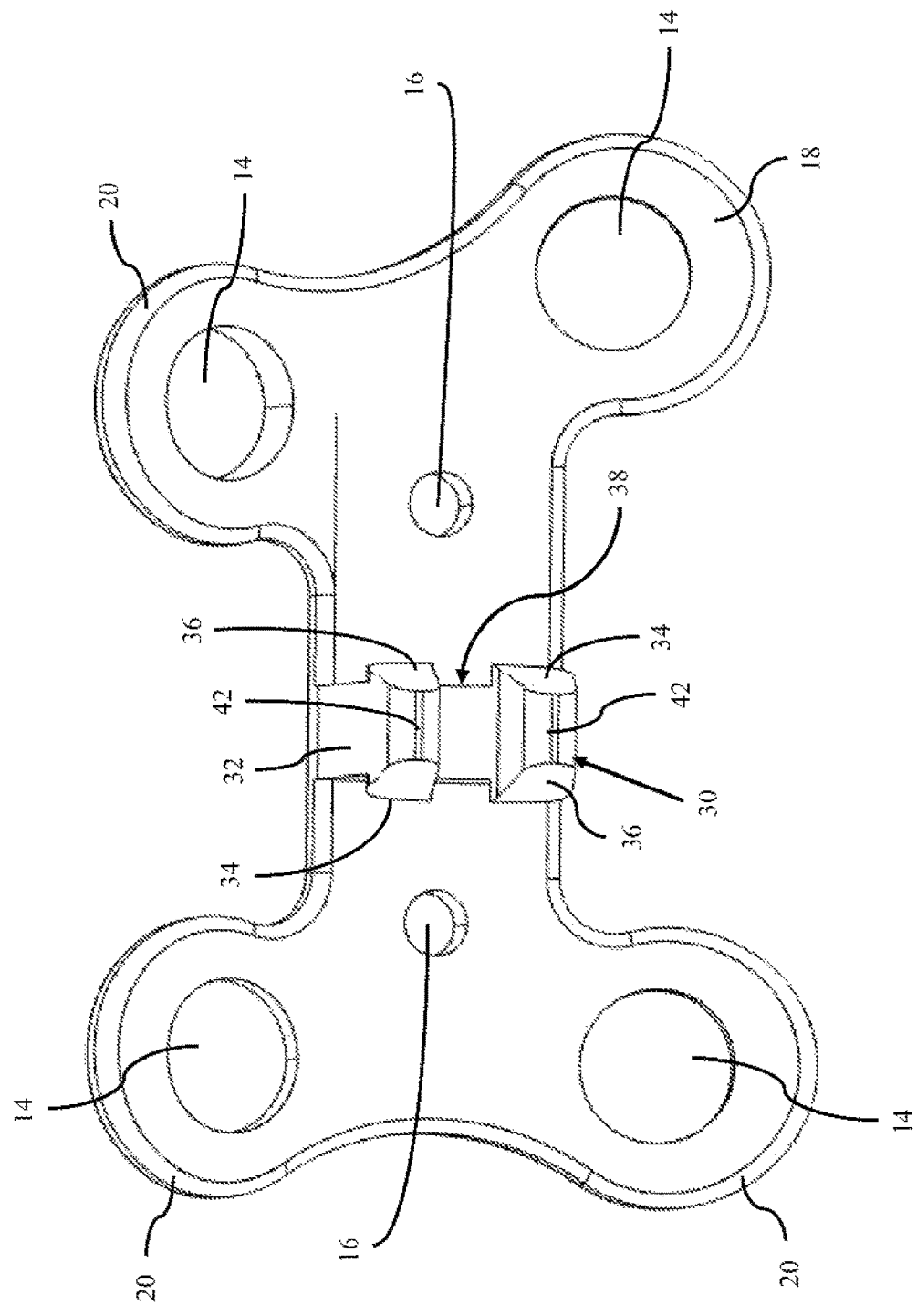
FIG. 5 is a bottom view of the plate of FIG. 1, in accordance with an aspect of the present invention.
Figure 6:
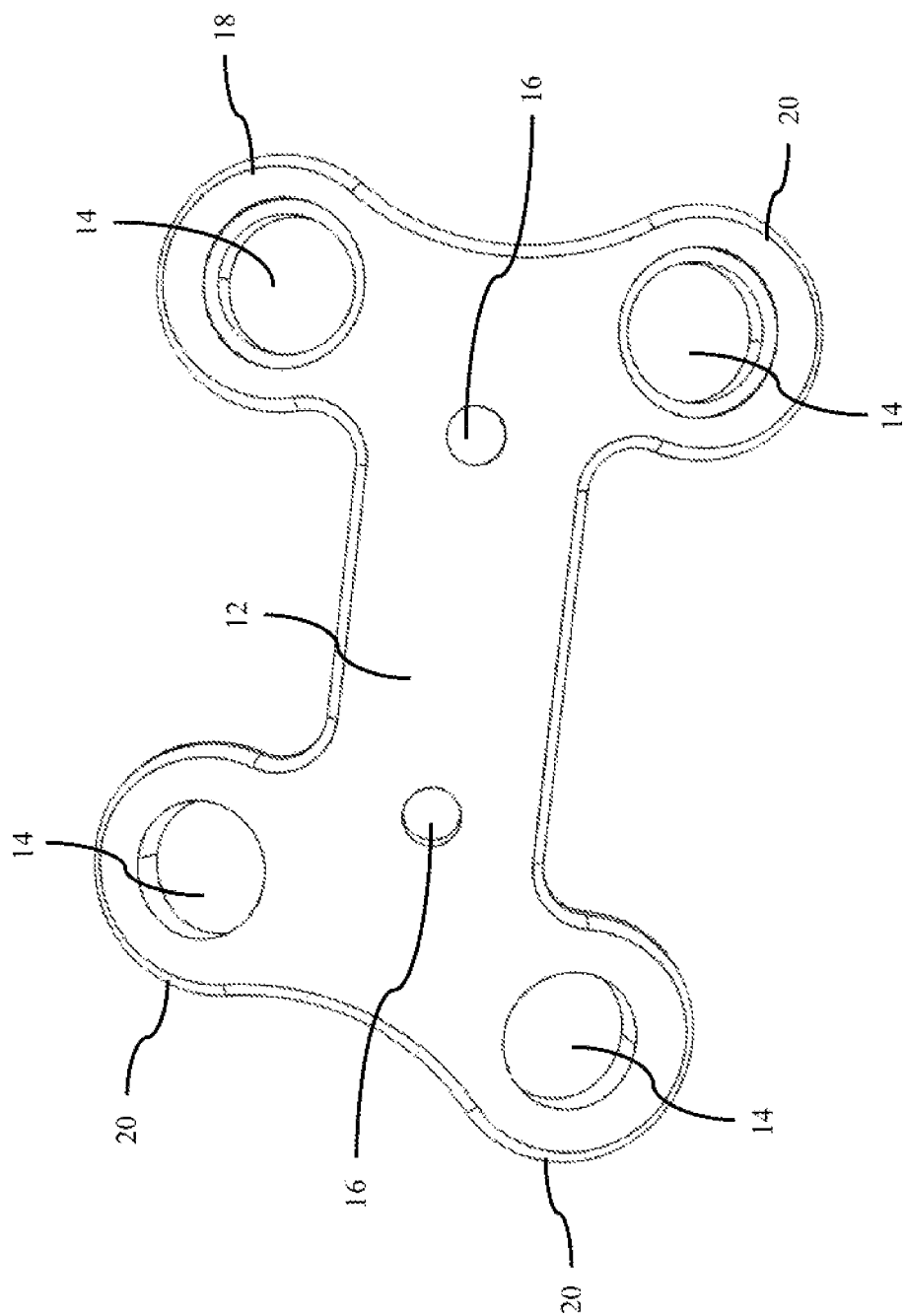
FIG. 6 is a top view of the plate of FIG. 1, in accordance with an aspect of the present invention.

Referring to the drawings, wherein like reference numerals are used to indicate like or analogous components throughout the several views, and with particular reference to FIGS. 1-6, there is illustrated an exemplary embodiment orthopedic bone plate 10. The plate 10 may be, for example, a base opening wedge plate or BOW plate. The plate 10 may include a body 12 with one or more holes or screw holes 14, at least one opening 16, and a securing mechanism or locking mechanism 30. The body 12 may include a first end, a second end, and a central portion extending between the first end and second end. The plate 10 may have, for example, a longitudinal curvature for conforming to the bone(s) it is attached to. The plate 10 may also have, for example, a diametral curvature for conforming to the surface of the outer cortex of the bone or bones which the plate 10 is attached to, as shown in FIG. 2. For example purposes, the plate 10 is shown as being generally I-shaped (See FIG. 5) with a generally rectangular shaped body 12 and including two pairs of rounded lobes, arms, ears, tabs, or the like. However, other plate shapes are also contemplated for use and such other shapes may be necessary to address certain clinical situations.

With continued reference to FIGS. 1-6, the screw holes 14 may be located in a first pair of rounded lobes and a second pair of rounded lobes extending from body 12. For example, the first pair of lobes at the first end of the body 12 may include a first lobe 18, which is offset from a second lobe 20, while the second pair of lobes at the second end of the body 12 may have two parallel oriented second lobes 20. Thus, in the depicted embodiment there are preferably four screw holes 14 corresponding to the four lobes 18, 20. However, it is contemplated that a plurality of screw holes may be present in each lobe 18, 20. The one or more screw holes 14 may be threaded or non-threaded holes. The one or more screw holes 14 in the second pair of rounded lobes, for example, the proximal lobes, may be, for example, angled to receive a fastener, such as, a bone screw, which may be positioned to converge toward the securing mechanism 30. By orienting the fasteners in the proximal lobes toward the securing mechanism 30, the fasteners may avoid the joint cartilage that curves inward in the patient's joint. Thus, the surgeon may be able to position the plate 10 to make the osteotomy more proximal to improve healing due to the osteotomy being in a more vascular space.

The at least one opening 16 may be located along the longitudinal axis of the plate 10 in the body 12. In the depicted embodiment, for example, the plate 10 may include two openings 16 aligned along the center of the body 12 where the first and second pairs of rounded lobes extend out from the body 12. The two openings 16 may be, for example, used for inserting temporary fixation pins, olive wires, k-wires or the like during attachment of the plate 10 to the patient's bone or bones.

The securing mechanism 30, as shown in FIGS. 1-6, may include a base portion 32 extending inferior from a bone contacting surface of the central portion of the body 12. The securing mechanism 30 may also include at least two opposing extension members or wedge portions 34 projecting from the base portion 32 to an insertion end 42. The extension members 34 may include at least two wedges 36 and a cavity or intermediate cavity 38. In the depicted embodiment, the extension members 34 may include, for example, two wedges 36 and a cavity 38. The at least two extension members 34 may also include, a plurality of retaining members, shoulders, or lips 40. The plurality of shoulders 40 may be positioned along a side of each of the extension members 34 or protrude away from the extension members 34 with for example one shoulder 40 in a proximal direction and a second shoulder 40 in a distal direction. The insertion end 42 is positioned at an end of each of the plurality of retaining members 40 opposite the base portion 32. The at least one wedge 36 of the wedge portion 34 may be tapered or angled from the lips 40 to the insertion end 42 as it extends inferiorly from the base 32. The securing mechanism 30 may be tapered or angled, for example, in both the proximal-distal direction and medial-lateral direction, as shown in FIGS. 1 and 2, respectively. It is also contemplated that the securing mechanism 30 may only be tapered or angled in one direction. The above described securing mechanism 30 may also be incorporated into other orthopedic bone plates which may be used to secure at least two bones together in a desired orientation after, for example, an osteotomy.

Figure 7:
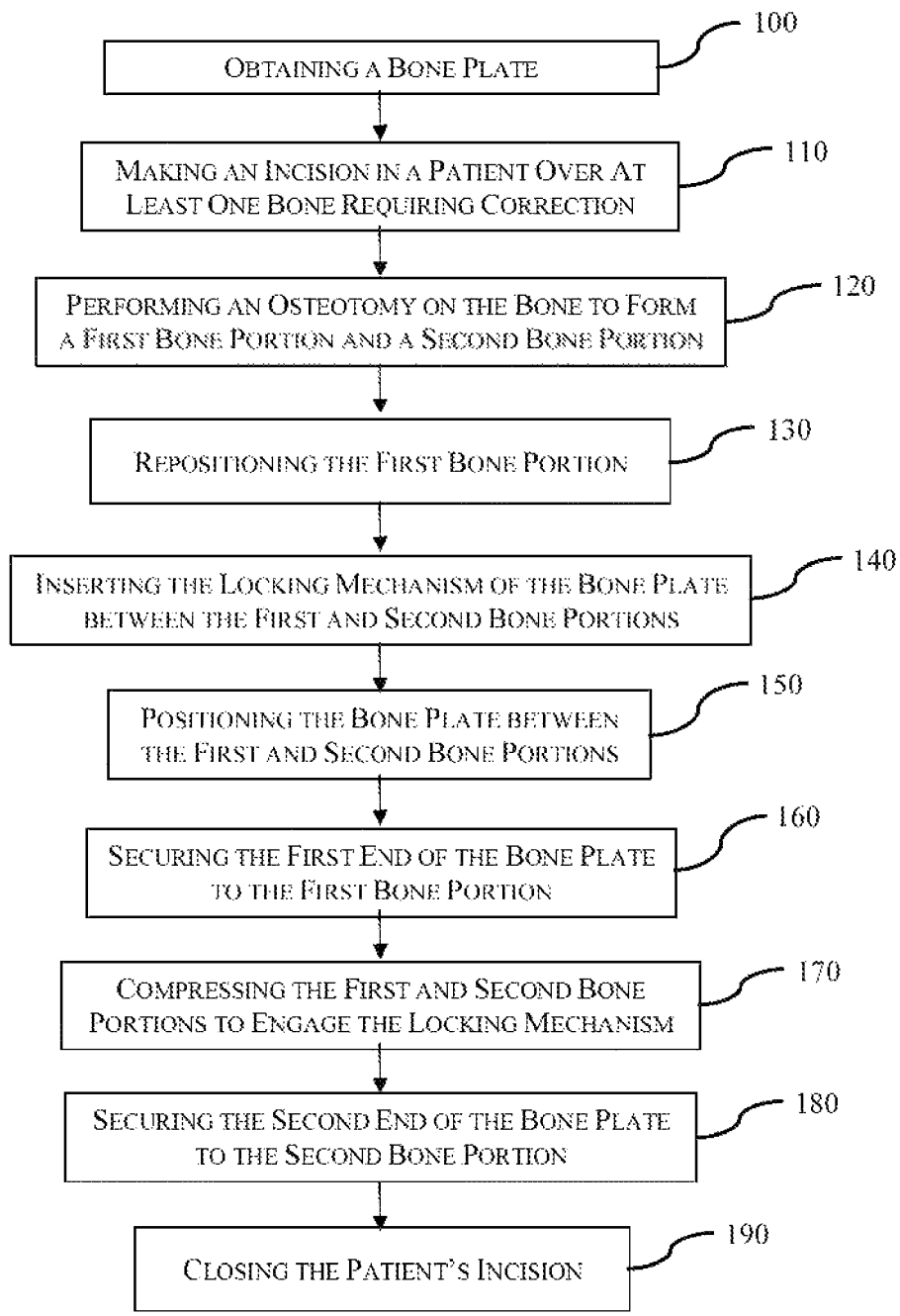
FIG. 7 depicts one embodiment of a method for inserting a bone plate, in accordance with an aspect of the present invention.
Figure 8:
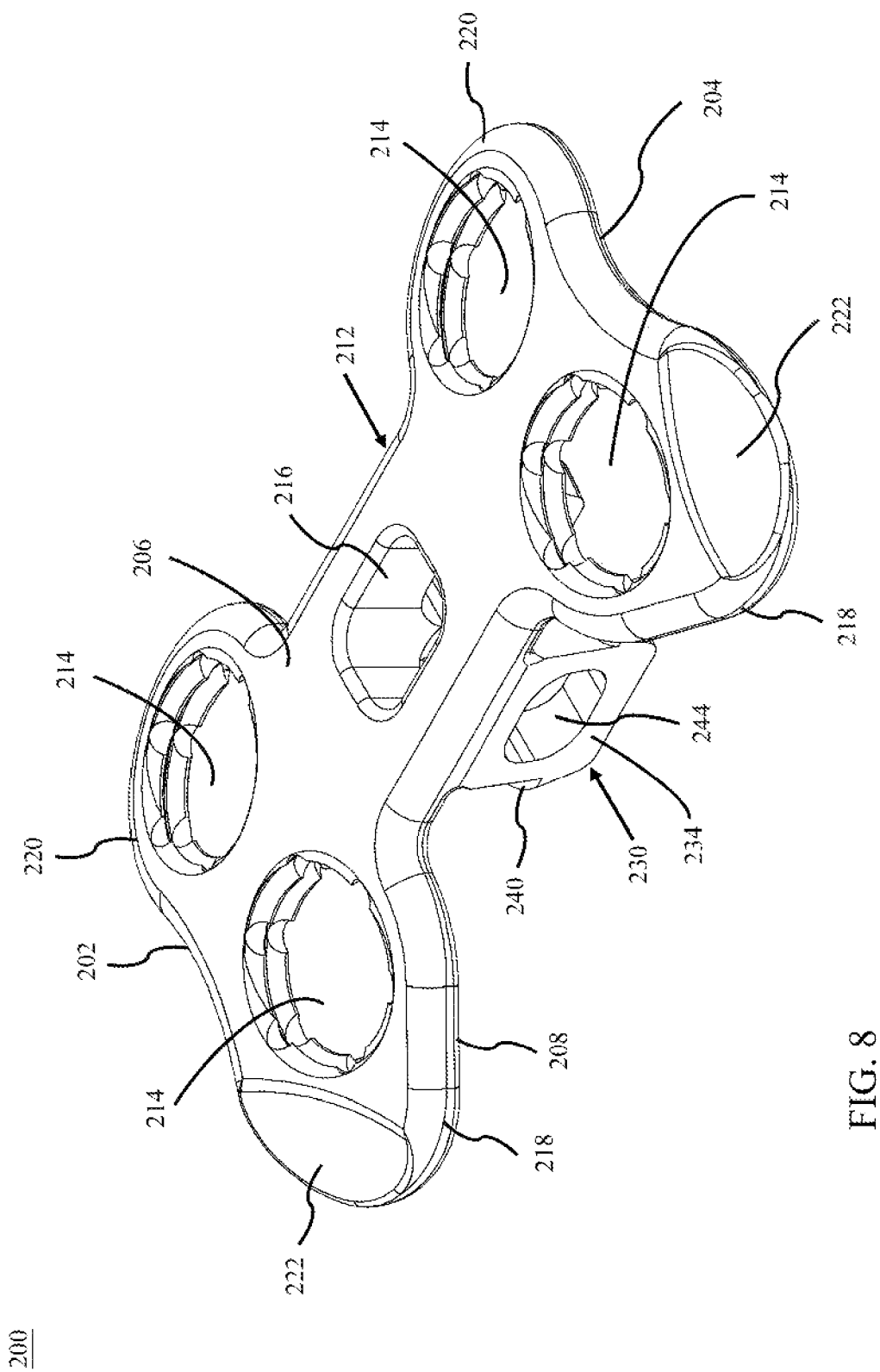
FIG. 8 is a top perspective view of another orthopedic bone plate, in accordance with an aspect of the present invention.

As depicted in FIG. 7, the method for insertion of the orthopedic plate 10 includes, the surgeon making an incision in the patient to perform an osteotomy on the bone or bones requiring correction. During the osteotomy a first bone may be cut leaving a connection between the two portions of the first bone. The connection between the two portions of the first bone may act as a hinge. If the osteotomy was, for example, being performed on the foot bones, then the hinge may be an intact lateral cortex. Once the osteotomy is completed, the first bone may be repositioned and the plate 10 may be inserted. When the plate 10 is inserted into the patient, the securing mechanism 30 of the plate 10 may be slid into place between the portions of the bone or bones created by the osteotomy.

After the securing mechanism 30 and plate 10 are inserted into the patient the surgeon may position the plate 10 in a desired position within the osteotomy and over the bones. A temporary fixation pin, olive wire, k-wire or the like may be inserted into one of the openings 16 to hold the plate 10 in the desired position in a first portion of the bone. In the preferred method olive wires are used because the olive wires contain a stopper which holds the plate 10 down on the bone while the fasteners are inserted. Alternative temporary fixation mechanisms that include a stopper or means to hold the plate 10 to the bones are also contemplated. Then plate 10 may be fastened to the first portion of the bone using at least one fastener, such as a bone screw. In the depicted embodiment, two fasteners would be inserted into two of the openings 14 on one end of the plate 10. Once the two fasteners are inserted and the plate is secured to the bone at one end the temporary fixation pin may be removed.

The surgeon may then move or compress the bones or portions of the bone to a desired position and insert a temporary fixation pin, olive wire, k-wire or the like into the other opening 16 to hold the plate 10 in the desired position on the second portion of the bone. As the bones are moved the cortical wall on both sides of the osteotomy engages the lips 40 of the securing mechanism 30. The plate 10 may then be fastened at the second end to the second portion of the first bone using at least one fastener, such as a bone screw. In the depicted embodiment, two fasteners would be inserted into the two openings 14 on the second end of the plate 10. After the fasteners are inserted into the bone and plate 10 is secured, the temporary fixation pin may be removed. Once the fasteners are inserted into both ends of the plate 10 securing the plate 10 to the bone, the securing mechanism 30 is engaging the cortical wall on both sides of the osteotomy. The engagement of the cortical wall by the securing mechanism 30 prevents the securing mechanism 30 from backing out of the osteotomy and holds the plate 10 down on the bone. Once the plate 10 is secured to the bone, the surgeon may then close the patient's incision.

In one embodiment, as shown in FIG. 7, a method for inserting a bone plate in accordance with one or more aspects of the present invention may include, for instance: obtaining the bone plate 100; making an incision in a patient over at least one bone requiring correction 110; performing an osteotomy on the at least one bone to form a first bone portion and a second bone portion 120; repositioning the first bone portion 130; inserting the securing mechanism of the bone plate between the first bone portion and the second bone portion 140; positioning the bone plate between the first bone portion and the second bone portion 150; securing the first end of the bone plate to the first bone portion 160; moving the first bone portion and the second bone portion to a desired position to engage the securing mechanism 170; securing the second end of the bone plate to the second bone portion 180; and closing the incision in the patient 190.

Figure 9:
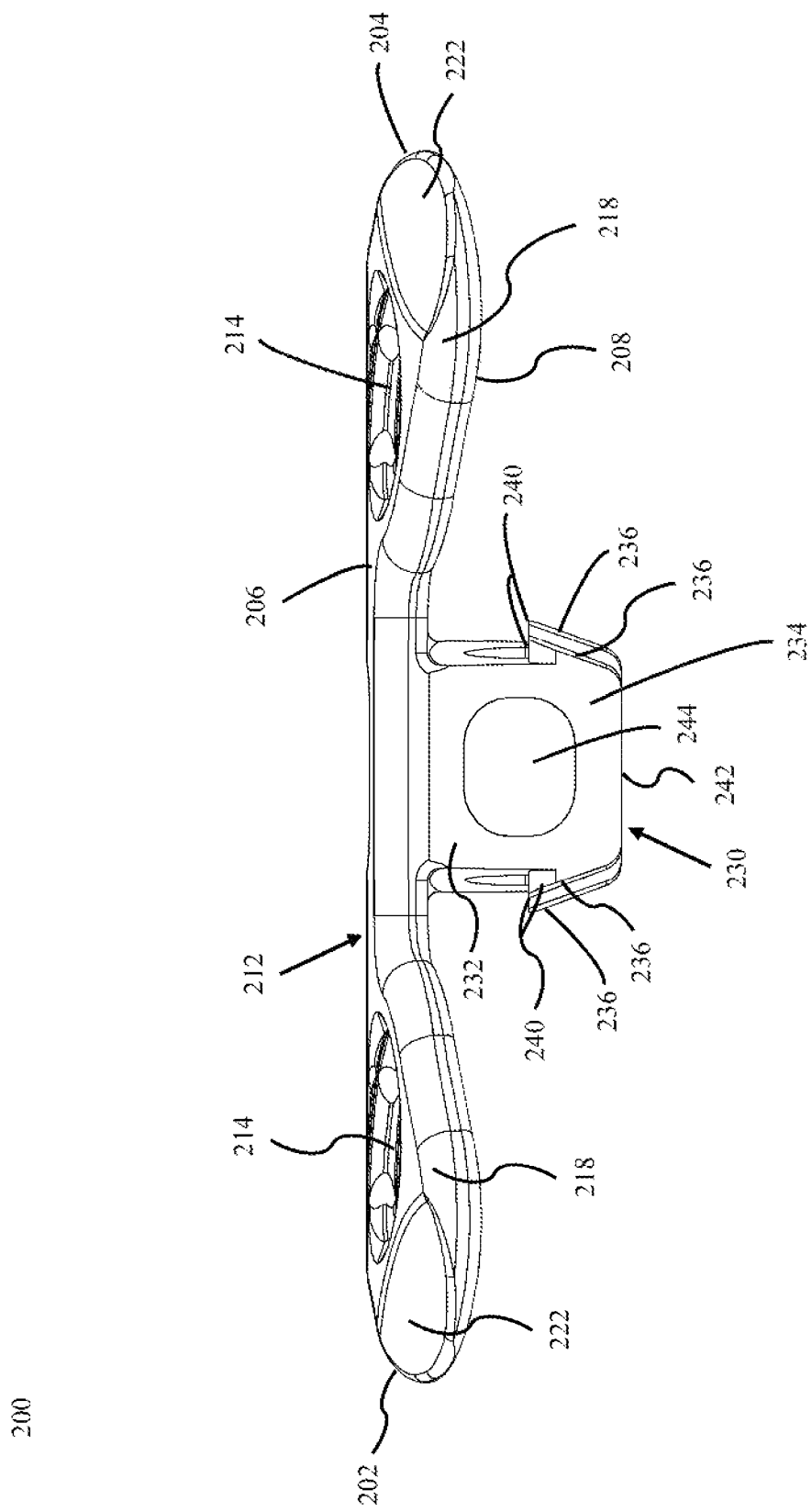
FIG. 9 is a side view of the orthopedic bone plate of FIG. 8, in accordance with an aspect of the present invention.
Figure 10:
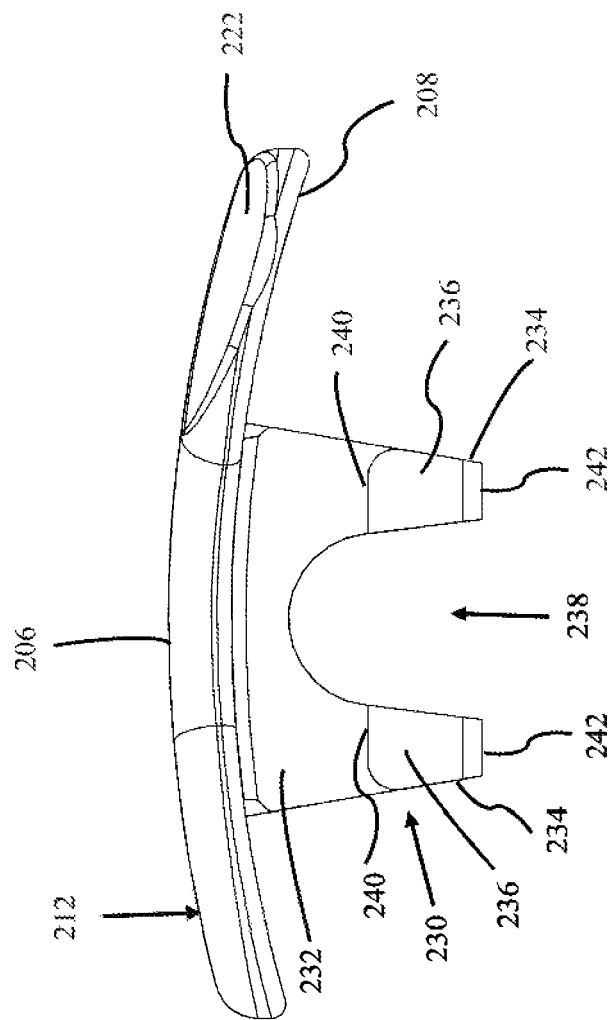
FIG. 10 is an end view of the orthopedic bone plate of FIG. 8, in accordance with an aspect of the present invention.
Figure 11:
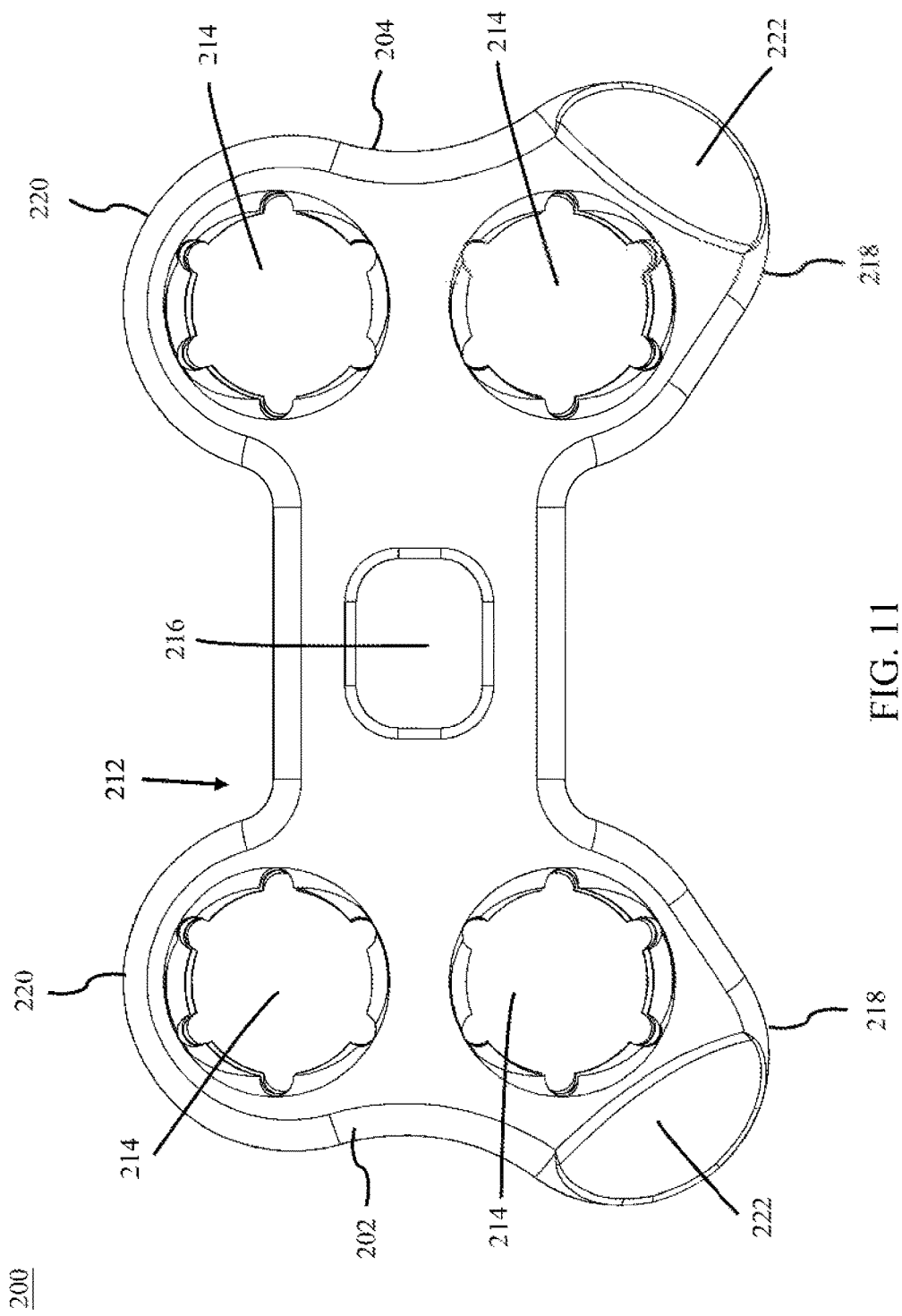
FIG. 11 is a top view of the orthopedic bone plate of FIG. 8, in accordance with an aspect of the present invention.

Another orthopedic bone plate 200 is shown in FIGS. 8-13. The bone plate 200 may include, for example, a body 212 and a securing or locking mechanism 230. The body 212 may have a first end 202, a second end 204 opposite the first end 202, and a central portion extending between the first end 202 and the second end 204. The body 212 may also include a top surface 206 and a bottom surface 208. Similar to the bone plate 10, the bone plate 200 may have, for example, a longitudinal curvature for conforming to the bone(s) the plate 200, as shown in FIG. 9, is attached to and a diametral curvature for conforming to the surface of the outer cortex of the bone or bones to which the plate 200 is attached, as shown in FIG. 10.

With continued reference to FIGS. 8-13, the body 212 may include one or more holes or screw holes 214 and an opening 216. The screw holes 214 may be positioned in a first pair of rounded lobes or ears and a second pair of rounded lobes or ears extending from the body 212. For example, the first pair of lobes at the first end 202 of the body 212 may include a first lobe 218 which is offset from a second lobe 220 and the second pair of lobes at the second end 204 of the body 212 may also include a first lobe 218 which is offset from a second lobe 220. The first lobes 218 may each include a ramped portion 222. The ramped portions 222 may allow for surrounding soft tissue to slide across the bone plate 200 and eliminate potential in vivo irritation. Thus, in the depicted embodiment there are four screw holes 214, one positioned in each of the lobes 218, 220. However, it is also contemplated that a plurality of screw holes 214 may be positioned in each lobe 218, 220. The one or more screw holes 214 may be threaded or non-threaded. Further, one or more of the screw holes 214 may be, for example, angled to receive a fastener, such as, a bone screw, which may be positioned to converge toward the securing mechanism 230. The screw holes 214 may be oriented toward the securing mechanism 230 to, for example, avoid any critical anatomic features or optimize placement on the bone to facilitate healing.

The opening 216 may be located in the body 212 between the first end 202 and the second end 204. The opening 216 may extend between the top surface 206 and the bottom surface 208 of the body 212. The opening 216 may be positioned along the longitudinal axis of the plate 200 over the securing mechanism 230. The opening 216 may allow for visualization of the wedge or graft material inserted beneath the bone plate 200. The opening 216 may also allow for the insertion of bone graft material between the two bones to assist with bone fusion after the procedure is complete.

Figure 12:
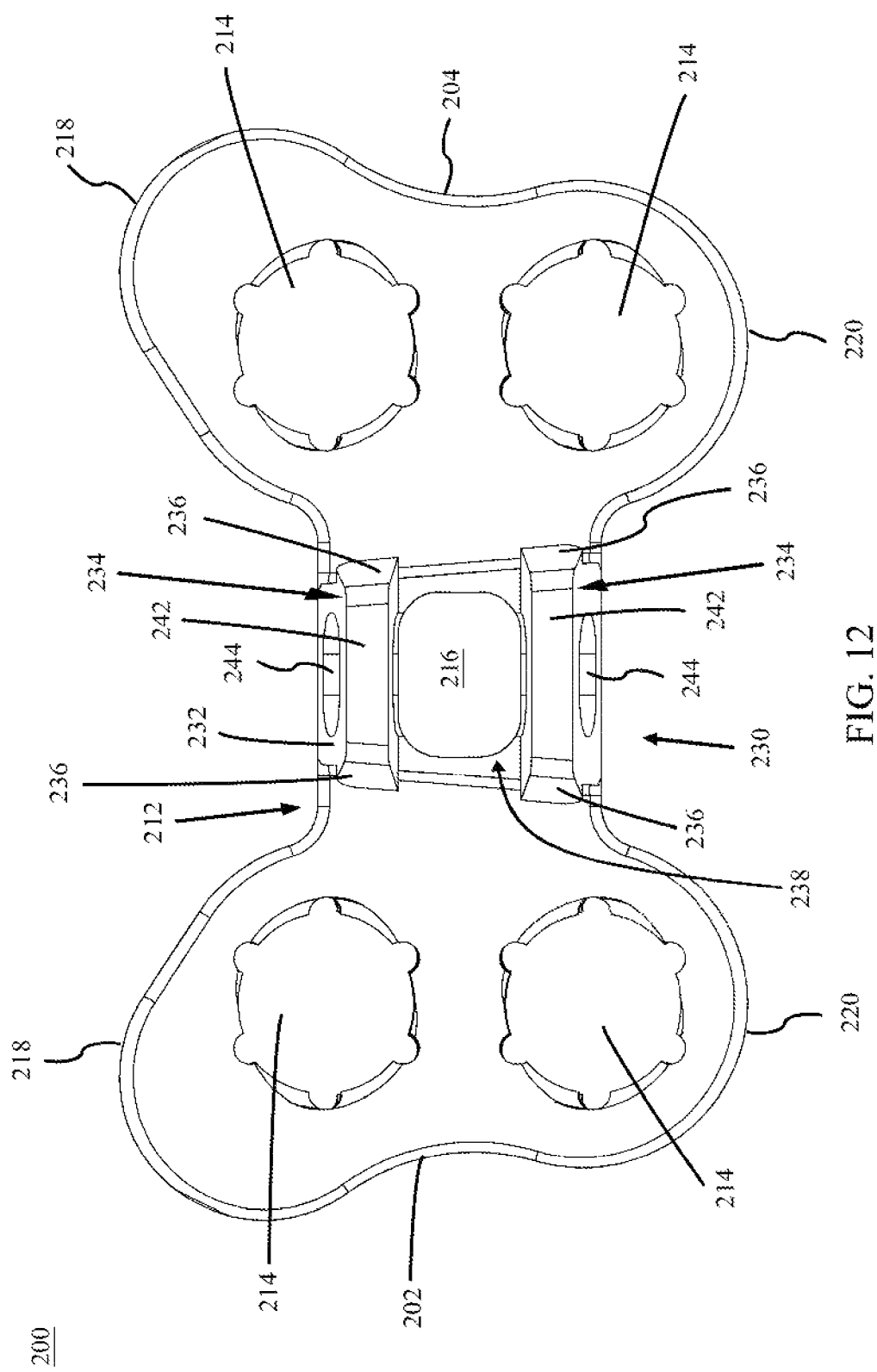
FIG. 12 is a bottom view of the orthopedic bone plate of FIG. 8, in accordance with an aspect of the present invention.
Figure 13:
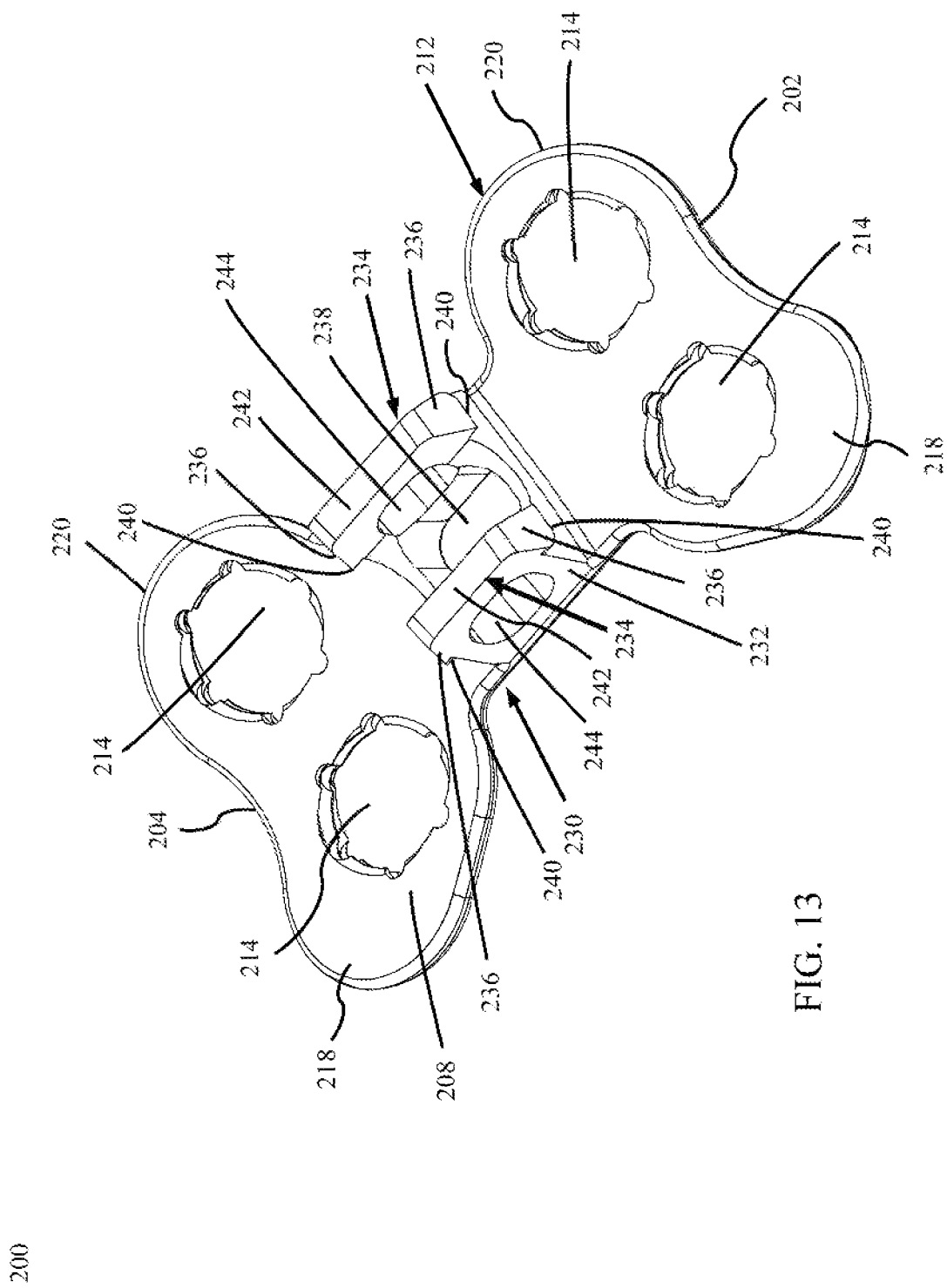
FIG. 13 is a bottom perspective view of the orthopedic bone plate of FIG. 8, in accordance with an aspect of the present invention.

The securing mechanism 230, as shown in FIGS. 8-10 and 12-13, may include a base portion 232 extending in an inferior direction from the bottom bone contacting surface 208 of the central portion of the body 212. The securing mechanism 230 may also include at least two opposing extension members or wedge portions 234 projecting from the base portion 232 to an insertion end 242. The extension members 234 may include at least two wedges 236 and a cavity or intermediate cavity 238 positioned between the extension members 234. Each of the extension members 234 may include an opening 244 extending into the cavity 238. In the depicted embodiment, the extension members 234 may include, for example, two wedge portions 236 and a cavity 238. The at least two extension members 234 may also include, a plurality of retaining members, shoulders, or lips 240. The plurality of shoulders 240 may be positioned along a side of each of the extension members 234 or protrude away from the extension members 234 with, for example, one shoulder 240 in a proximal direction and a second shoulder 240 in a distal direction. The insertion end 242 is positioned at an end of each of the plurality of retaining members, shoulders, or lips 240 opposite the base portion 232. The at least one wedge 236 of the wedge portion 234 may be tapered or angled from the lips 240 to the insertion end 242 as it extends inferiorly from the base 232. The securing mechanism 230 may be tapered or angled from the bottom surface 208 of the bone plate 200 to the insertion end 242, for example, in a proximal-distal direction and a medial-lateral direction, as shown in FIGS. 9 and 10. Further, the base portion 232 of the securing mechanism 230 may be tapered or angled, for example, along the bottom surface 208 of the bone plate 200 from a first side to a second side, such as in a medial-lateral direction, as shown in FIGS. 12 and 13. The extension members 234 of the bone plate 200 with a tapered base portion 232 will have, for example, two different lengths in a proximal-distal direction. It is also contemplated that the securing mechanism 230 may be tapered or angled in only one direction or any combination of directions discussed above. The above described securing mechanism 230 may also be incorporated into other orthopedic bone plates which may be used to secure at least two bones together in a desired orientation after, for example, an osteotomy.

The method for insertion of an orthopedic plate, as described above with reference to FIG. 7, may also be performed using the orthopedic plate 200. The plate 200 with the tapered or angled securing mechanism 230 may be used for certain indications, for example, flatfoot, posterior tibial tendon dysfunction, proximal tibia osteotomy, distal tibia osteotomy, or any other indication using a wedge plate. The plate 200 with the tapered securing mechanism 230 of FIGS. 12 and 13 may be used to release pressure on the plantar aspect of the osteotomy and prevent gapping that may occur dorsally when a parallel securing mechanism, such as, securing mechanism 30 is used. The plate 200 may be used, for example, with an Evans osteotomy procedure to match the "V" shape created by distraction on the lateral wall.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An orthopedic plate, comprising:
   a body with a first end, a second end, and a central portion extending between the first end and the second end;
   a first pair of lobes at the first end;
   a second pair of lobes at the second end; and
   a securing mechanism extending away from a bottom surface of the central portion, wherein the securing mechanism comprises:
     a base portion extending between a medial side and a lateral side of the body, the base portion including a proximal end coupled to the body and a distal end; and
     at least two opposing extension members projecting from the distal end of the base portion;
     wherein each of the two opposing extension members comprise at least two retaining members, the at least two retaining members are positioned along an end of each of the two opposing extension members, and wherein a first retaining member of the at least two retaining members extends away from the extension members toward the first end of the body and a second retaining member of the at least two retaining members extends away from the extension members toward the second end of the body.

2. The orthopedic plate of claim 1, wherein the base portion is monolithic.

3. The orthopedic plate of claim 2, wherein the securing mechanism further comprises:
   a cavity positioned between the at least two opposing extension members.

4. The orthopedic plate of claim 3, wherein the at least two opposing extension members further comprise an insertion end positioned at an end of each of the at least two retaining members opposite the base portion, and wherein the insertion ends are blunt.

5. The orthopedic plate of claim 4, wherein the at least two opposing extension members are tapered from the at least two retaining members to the insertion end.

6. The orthopedic plate of claim 5, wherein the at least two opposing extension members are tapered in a proximal-distal direction from the distal end of the base portion to the insertion end, and wherein the base portion and the at least two opposing extension members are tapered in a medial-lateral direction from a bottom surface of the body to the insertion ends of the at least two opposing extension members.

7. The orthopaedic plate of claim 3, wherein the cavity is curved between the two opposing extension members.

8. The orthopedic plate of claim 1, further comprising:
   at least one hole in the first end of the body; and
   at least one hole in the second end of the body.

9. The orthopedic plate of claim 8, wherein the at least one hole in the first end comprises at least one hole in the first pair of lobes and the at least one hole in the second end comprises at least one hole in the second pair of lobes.

10. The orthopedic plate of claim 9, wherein each of the lobes in the second pair of lobes includes at least one hole and each of the at least one holes is angled toward the securing mechanism.

11. The orthopedic plate of claim 1, wherein the first pair of lobes includes a first lobe offset from a second lobe and the second pair of lobes includes a first lobe oriented parallel to a second lobe.

12. The orthopedic plate of claim 1, wherein the body has a longitudinal curvature from the first end to the second end.

13. The orthopedic plate of claim 12, wherein the body has a diametral curvature from the medial side to the lateral side.

14. A bone plate securing mechanism, wherein the securing mechanism is coupled to a bone plate and includes a body portion comprising:
   a base portion projecting from the body portion of the bone plate and extending between a medial side and a lateral side of the body portion of the bone plate, wherein the base portion is continuous between the medial side and the lateral side; and
   two opposing extension members projecting from a distal end of the base portion, wherein each of the two opposing extension members comprise:
     at least two shoulder portions positioned along an end of the two opposing extension members, wherein a first shoulder portion of the at least two shoulder portions projects in a first direction, and wherein a second shoulder portion of the at least two shoulder portions projects in a second direction; and
     an insertion end positioned at a distal end of each of the two opposing extension members.

15. The bone plate securing mechanism of claim 14, wherein a cavity is defined by the two opposing extension members, and wherein a bottom portion of the cavity is curved between the two opposing extension members.

16. The bone plate securing mechanism of claim 15, wherein the insertion end of the two opposing extension members is rounded.

17. The bone plate securing mechanism of claim 16, wherein the at least two opposing extension members are angled from the at least two retaining members to the insertion end.

18. The bone plate securing mechanism of claim 17, wherein the at least two opposing extension members are angled in a proximal-distal direction from the distal end of the base portion to the insertion end, and wherein the base portion and the at least two opposing extension members are tapered in a medial-lateral direction from a proximal end of the base portion to the insertion ends of the at least two opposing extension members.

* * * * *